(12) United States Patent
Piraee

(10) Patent No.: US 9,486,464 B2
(45) Date of Patent: Nov. 8, 2016

(54) COMPOSITION AND METHOD OF MANUFACTURE

(75) Inventor: Mahmood Piraee, Montreal (CA)

(73) Assignee: Persavita Ltd, Cambridge (GB)

( * ) Notice: Subject to any disclaimer, the term of this patent is extended or adjusted under 35 U.S.C. 154(b) by 95 days.

(21) Appl. No.: 13/819,173

(22) PCT Filed: Aug. 25, 2011

(86) PCT No.: PCT/EP2011/004254
§ 371 (c)(1),
(2), (4) Date: Feb. 26, 2013

(87) PCT Pub. No.: WO2012/025229
PCT Pub. Date: Mar. 1, 2012

(65) Prior Publication Data
US 2013/0156746 A1    Jun. 20, 2013

(30) Foreign Application Priority Data

Aug. 27, 2010  (GB) .................................. 1014340.2
Jan. 19, 2011  (GB) .................................. 1100925.5

(51) Int. Cl.
| | | |
|---|---|---|
| A61K 31/7024 | (2006.01) | |
| A61K 31/05 | (2006.01) | |
| A61K 36/88 | (2006.01) | |
| A61K 31/047 | (2006.01) | |
| A61K 31/122 | (2006.01) | |
| A61K 31/202 | (2006.01) | |
| A61K 31/355 | (2006.01) | |
| A61K 31/375 | (2006.01) | |
| A61K 31/59 | (2006.01) | |
| A61K 33/30 | (2006.01) | |
| A61K 33/34 | (2006.01) | |

(52) U.S. Cl.
CPC ......... *A61K 31/7024* (2013.01); *A61K 31/047* (2013.01); *A61K 31/05* (2013.01); *A61K 31/122* (2013.01); *A61K 31/202* (2013.01); *A61K 31/355* (2013.01); *A61K 31/375* (2013.01); *A61K 31/59* (2013.01); *A61K 33/30* (2013.01); *A61K 33/34* (2013.01); *A61K 36/88* (2013.01)

(58) Field of Classification Search
None
See application file for complete search history.

(56) References Cited

U.S. PATENT DOCUMENTS

| | | |
|---|---|---|
| 6,573,299 B1 | 6/2003 | Petrus |
| 2005/0214383 A1* | 9/2005 | Bubnis .................. A23L 1/0017 424/641 |
| 2007/0149466 A1* | 6/2007 | Milburn .................. A23L 1/293 514/43 |
| 2008/0254140 A1* | 10/2008 | Widder .................. A61K 31/10 424/630 |
| 2009/0169585 A1 | 7/2009 | Sardi |
| 2010/0210572 A1 | 8/2010 | Eidenberger |

FOREIGN PATENT DOCUMENTS

| | | |
|---|---|---|
| CA | 2809071 A1 | 3/2012 |
| CN | 101 062 339 A | 10/2007 |
| CN | 101 279 030 A | 10/2008 |
| CN | 101 297908 A | 11/2008 |
| CN | 101 361 892 A | 2/2009 |
| CN | 101 597 554 A1 | 12/2009 |
| DE | 19948652 A1 | 4/2001 |
| GB | 2483121 A | 2/2012 |
| IN | 2770/DELNP/2013 | 11/2014 |
| WO | 2007/020673 A1 | 2/2007 |
| WO | 2012025229 A1 | 3/2012 |
| WO | 2012025229 A8 | 10/2012 |

OTHER PUBLICATIONS

Sooft "Protezione Retina product description", Company webpage, copyright 2007.*
Lage et al. "Quantification of saffron (*Crocus sativus* L.) metabolites crocins, picrocrocin and safranal for quality determination of the spice grown under different environmental Moroccan condtions", Scientia Horticulturae 121: 366-373, 2009.*
Merriam-Webster Online Dictionary, definition of dose, accessed 2013.*
Sooft italia, Ophthalmic Pharmaceutical Company, Company webpage, copyright 2007, as captured on Jun. 30, 2009.*
Sooft italia, PDF of the product list in Italian, Company webpage, copyright 2007, as captured on Jun. 30, 2009.*
Sooft italia, PDF of the product list, relevant sections machine translated, Company webpage, copyright 2007, as captured on Jun. 30, 2009.*
Savrieno "Is a patent war about to erupt between Evolva and Stevia First?", Seeking Alpha online magazine, first page, published online Jan. 14, 2014.*
Daniells "Evolve outlines timetable for fermentation-derived vanillin, stevia and saffron", Food Navigator—USA.com online magazine, published online Apr. 10, 2013.*
Falsini et al. "Influence of saffron supplementation on retinal flicker sensitivity in early age-related macular degeneration" Investigative Ophthalmology and Visual Science 51: 6118-24, 2010, published online Aug. 4, 2010.*

(Continued)

*Primary Examiner* — Emily Cordas
(74) *Attorney, Agent, or Firm* — Ziegler IP Law Group, LLC

(57) ABSTRACT

A dietary supplement composition includes a synergistic combination of saffron and resveratrol for providing antioxidant and gene modulation effects for preventing, ameliorating and/or reducing a rate of development and progression of age-related macular degeneration (AMD). Optionally, the combination is supplemented with one or more further ingredients: fish oil, Zinc, Copper, vitamin C, vitamin E, lutein, zeaxanthin. The combination is beneficially provided as a composition which is useful for reducing a risk of developing, and/or for reducing a rate of progression of age-related macular degeneration, and/or for preventing age-related sight loss, and other age-related diseases.

6 Claims, 3 Drawing Sheets

(56) References Cited

OTHER PUBLICATIONS

Figure 1:
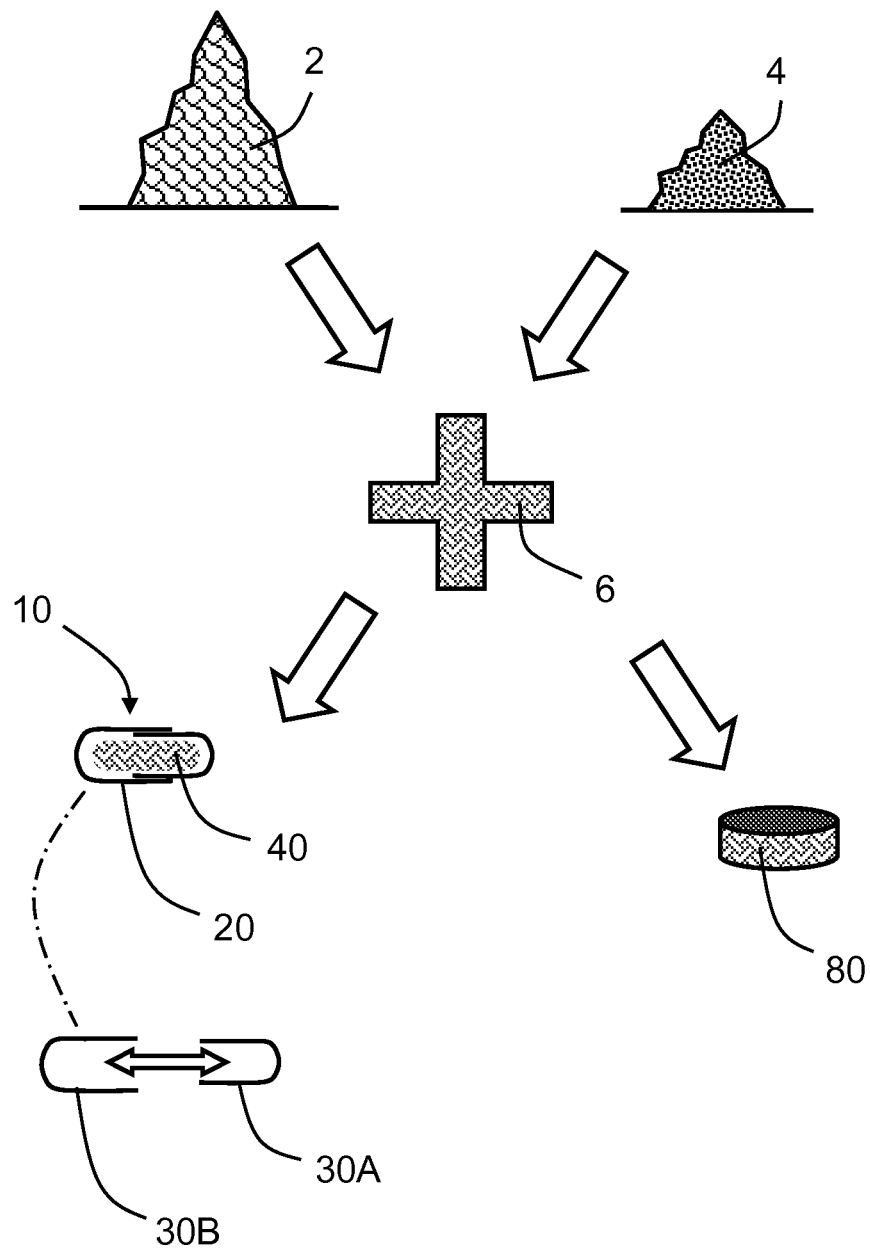

King et al. "Resveratrol reduces oxidation and proliferation of human retinal pigment epithelial cells via extracellular signal-regulated kinase inhibition", Chemico-Biological Interactions 151: 143-149, 2005.*
Chew et al. "Lutein + zeaxanthin and omega-3 fatty acids for age-related macular degeneration: The age-related eye disease study 2 (AREDS2) randomized clinical trial", JAMA 309(19): 2005-2015, 2013.*
Combined Search and Examination Report received for United Kingdom Patent Application No. GB1100925.5, dated Apr. 7, 2011, 9 pages.
International Preliminary Report on Patentability and Written Opinion received for International Patent Application No. PCT/EP2011/004254, dated Mar. 14, 2013, 7 pages.
International Search Report received for International Patent Application No. PCT/EP2011/004254, dated Oct. 13, 2011, 4 pages.
Synergistic cytoprotective effect of Crocin (CRN) and Resveratrol (RSV) on Primary Human Retinal Pigmentepithelium (RPE) cells; M Kernt et al; https://www.thieme-connect.de/ejournals/abstract/10.1055/s-0032-132055; Planta Med 2012; 78-PF7; DOI: 10.1055/s-0032-1320553; 2012.
Synergism Between Resveratrol and Crocin for Protection of Human Neuroblastoma SHSY-5Y Cells against Oxidative Stress; D Albani et al. https://www.thieme-connect.com/ejournals/abstract/10.1055/s-0033-1348612; Planta Med 2013; 79-PH22; DOI: 10.1055/s-0033-1348612; 2013.
"The time course of action of two neuroprotectants, dietary saffron and photobiomodulation, assessed in the rat retina." Author Di Marco et al. Publisehd Sep. 30, 2013, 13 pages.
"Molecular mechanisms of retinal pigment epithelium damage and development of age-related macular degeneration." Author: Kinnunen et al. Published 2012 "Acta Ophthalmologica", 11 pages.

"Protective Effect of Crocin against Blue Light-and White Light-Mediated Photoreceptor Cell Death in Bovine and Primate Retinal Primary Cell Culture." Author: Laabich et al. Published in IOVS, Jul. 2006, vol. 47, No. 7, 8 pages.
"Antioxidant Effect of Trans-Resveratrol in Cultured Human Retinal Pigment Epithelial Cells." Author Pintea et al. Published in Journal of Ocular Pharmacology and Therapeutics vol. 27, No. 4, 2011, 9 pages.
"Crocetin prevents retinal degeneration induced by oxidative and endoplasmic reticulum stresses via inhibition of aaspase activity." Author: Yamauchi et al. Published in the European Journal of Pharmacology Jan. 10, 2011, vol. 650 Issue 1 ISSN 0014-2999. 11 pages.
"The combination of resveratrol and CLA does not increase the delpidating effect of each molecule in 3T3-L1 adipocytes" Lasa et al. Nutricion Hospitalaria,ISSN: 0212-1611, vol. 26, No. 5, Sep.-Oct. 2011, 8 pages.
"Herb-Drug Interactions: Challenges and Opportunities for Improved Predictions" Brantley et al., The American Society for Pharmacology and Experimental Therapeutics, Received Oct. 4, 2013; accepted Dec. 11, 2013, Drug Metab Dispos 42:301-317, Mar. 2014, 17 pages.
"Combining Neuroprotectants in a Model of Retinal Degeneration: No Additive Benefit" Di Marco et al. PLoS One 9 (6): e100389. doi: 10.1371/journal.pone.0100389, Jun. 2014 vol. 6, 7 pages.
"Systemic treatment with resveratrol and/or curcumin reduces the progression of experimental periodontitis in rats" Correa et al., Journal of Periodonatal Research doi: 10.1111/jre.12382, 2016, Published by John Wiley & Sons Ltd.
"Drug interaction potential of resveratrol" Detampel et al., Drug Metabolism Reviews 1012; 44 (3):253-265, 2012 Informa Healthcare USA, Inc. ISSN 0360-2532 print/ISSN 1097-9883 online, DOI: 10.3109/03602532.2012700715, 14 pages.

* cited by examiner

COMPOSITION AND METHOD OF MANUFACTURE

TECHNICAL FIELD OF INVENTION

The present invention relates to dietary supplements for improving human health, for example to dietary supplements for reducing a risk of developing macular degeneration, for slowing its progression, and for preventing age-related sight loss as well as other age-related diseases. Moreover, the invention concerns methods of manufacturing aforesaid dietary supplements. Furthermore, the invention relates to methods of using aforesaid dietary supplements.

BACKGROUND TO THE INVENTION

Eye conditions tend to be linked to age, genetics, environment, tobacco abuse and diet. Most common eye conditions affecting the global population are age-related macular-degeneration (AMD), cataracts and xerophthalmia, the latter of which is caused by a deficiency of vitamin A, and which is a common cause of childhood blindness.

According to estimates by the World Health Organisation (WHO), more than two hundred and sixty million people around the world are affected by visual impairment, excluding blindness. Macular degeneration is more prevalent among senior adults and accounts for 7% of age-related conditions in people over the age of 50 years. According to a study published in the Indian Journal of Medical Sciences in 2007, the incidence of eye disease has been found to compound in humans at a mean age of 43.9 years.

The nutritional market for eye health products is dominated by dietary supplements, which comprised just over 66% of the market in the year 2007, according to a report by Frost & Sullivan analysts. Euromonitor estimates that eye health products account for 1% of total sales of the whole vitamins and dietary supplements market.

The market for eye health products in the USA is by far the most developed market, which is driven mainly by a greater acceptance and higher level of awareness of dietary supplements. Frost & Sullivan has estimated the US eye health ingredients market to be worth $138 (USD) million in the year 2008, with a compound annual growth rate (CAGR) of 5.3% from the year 2008 to the year 2015. The European market was valued at $43.4 (USD) million in the year 2007 with a CAGR of 10.5% from the year 2007 to the year 2014; such results are published at the following Internet website: see the website for nutraingredients.com/Product-Categories/Antioxidants-carotenoids/Unravelling-the-market-for-eye-health Age-related macular degeneration (AMD) is a leading cause of a loss of adult vision amongst citizens in developed countries. AMD accounts for more than 50% of blindness amongst citizens in the United States of America (USA). More than 1.8 million citizens in the USA are affected by AMD. Moreover, it is expected that there will be an increase of 50% by the year 2030 in a total number of citizens in the USA affected by AMD as reported by Huang et al., 2008: National Eye Institute, "Vision problems in the US 2006" see the website for [nei.nih.gov/eyedata].

Based on major clinical studies, particularly a recent AREDS1 study, a known nutritional supplement formulation has been developed that is now used as a standard of care in certain cases of dry AMD. The known formulation, namely AREDS1 formulation, is used daily to deliver the following nutrients:

| | |
|---|---|
| Vitamin C | 500 mg |
| Vitamin E | 400 International Units (IU) (268 mg) |
| Beta-carotene | 15 mg |
| Zinc | 80 mg (in the form of Zinc Oxide) |
| Copper | 2 mg (in the form of Cupric Oxide) |

Several variations of the AREDS1 formulation from different suppliers are now available in the market for AMD patients and/or for healthy individuals as eye health nutritional supplement. These formulations are developed based on the results of the AREDS1 study and the cumulative clinical evidence about health benefits of other anti-oxidative nutrients, omega-3 fatty acids and herbal extracts.

Vision loss in sufferers with AMD is attributable to a death of photoreceptors in a central region of a human retina. An early stage of pathogenesis giving rise to AMD is associated with degeneration of retinal pigment epithelial (APR) cells, which is responsible for degradation of photoreceptor outer segments that have been shed. Such a mechanism for vision loss has been reported by Sheu et al., 2010 (Sheu S J, Lui N C, Chen J L, "Resveratrol protects human retinal pigment epithelial cells from acrolein-induced damage", J. Ocul Pharmacol The 26(3): pp 231-236). Moreover, risk factors affecting development of AMD include an age greater than 50 years, Caucasian race, nutrition, smoking, cardiovascular disease, genetics, and sunlight exposure as reported in aforementioned Sheu et al., and also Thornton et al., 2005.

An average age of the population of the USA is increasing and therefore a total number of USA citizens with major eye disease is also correspondingly increasing. Although vision loss is becoming a major public health problem, contemporary therapy options for AMD are presently limited, and therefore, preventative interventions are needed to reduce a burden to society represented by vision loss as reported by Huang et al., 2008 (Huang L L, Coleman H R, Kim J, de Monasterio F, Wong W T, Schleicher R L, Ferris F L 3$^{rd}$, Chew E Y (2008), "Oral supplementation of lutein/zeaxanthin an omega-3 long chain polyunsaturated fatty acids in persons aged 60 years or older, with or without AMD", Invest Ophthalmol Vis Sci 49(9): pp. 3864-3869).

Nutritional supplements are contemporarily being used to an increasing extent for improving health and delaying age-related chronic diseases as reported by Marainin et al., 2009 (Maraini G, Williams S L, Sperduto R D, Ferris F L, Milton R C, Clemons T E, Rosmini F, Ferrigno L, 2009, "Effects of multivitamin/mineral supplementation on plasma levels of nutrients", Report No. 4 of the Italian-American clinical trial of nutritional supplemented and age-related cataract, Ann 1st Super Sanita 45(2), pp. 119-127), by Joseph et al., 2009 (Joseph J, Cole G, Head E, Ingram D, 2009, "Nutrition, brain aging, and neurodegeneration", J Neurosci 29(41), pp. 12795-12801), by Jones, 2007 (Jones A A, 2007, "Age related macular degeneration—should your patients be taking additional supplements?", Aust Fam Physician 36(12), pp. 1026-1028) and by Cangemi 2007. Use of nutritional supplements has given a hope for development of new remedies and therapies for ameliorating AMD and to decelerate its progress as a function of adult age, and for reducing risk of vision loss.

In a Chinese patent application no. CN101062339A (20071031), there is described a composition including saffron and stilbene. Stilbene pertains to a specific chemical class of compounds which have in common a core diarylethene chemical moiety; the class includes a wide range of chemical entities. There is further described that Polygonum

*multiforum* is a plant source of stilbene. More particularly, *Polygonum multiforum* is a source of 2,3,5,4'-tetrahydroxystilbene 2-O-β-D-glucopyranoside, namely stilbene glycoside. However, this combination does not show functional benefits provided by the present invention.

In a Chinese patent application no. CN101597554A, there is described an improvement of thick wine brewing technique in respect of foodstuffs, namely for preparing a restorative beverage, wherein saffron is employed merely as a colouring agent. Indeed, mixtures of fruits and spices have been used for centuries in the Middle East, without scientific and mechanism-based knowledge of any medicinal benefits arising therefrom.

Thus, from the foregoing, it will be appreciated that AMD is a major debilitating contemporary problem for millions of people around the World. A satisfactory solution has hitherto not been provided for the most prevalent form of the disease, known as dry AMD, which accounts for more than 90% of AMD cases, despite considerable research effort being devoted to try to find a solution.

SUMMARY OF THE INVENTION

The present invention seeks to provide a composition for improving health, and/or for preventing or reducing a rate of development or progression of age-related macular degeneration (AMD), or reducing risk of vision loss from AMD.

The present invention seeks to provide a composition, for example a dietary supplement, which is capable of providing general health benefits, especially amongst more elderly individuals, for example in respect of ameliorating age-related macular degeneration (AMD).

According to a first aspect of the present invention, there is provided a composition as defined in appended claim 1: there is provided a composition for improving health, characterized in that said composition includes a combination of resveratrol and saffron.

The invention is of advantage in that a combination of resveratrol and saffron provides synergistic benefits in reducing a severity of various age-related conditions, for example age-related macular degeneration (AMD).

Optionally, the composition is implemented in a ratio of concentration of resveratrol: saffron being in a range of 1:1 to 100:1.

Optionally, in respect of the composition, each dose of the composition includes in a range of 1 mg to 10000 mg resveratrol, and in a range of 0.2 mg to 2000 mg saffron powder or an equivalent extract of it. More optionally, each dose of the composition includes in a range of 5 mg to 5000 mg resveratrol, and in a range of 1 mg to 1000 mg saffron powder. Yet more optionally, each dose of the composition includes in a range 50 mg to 700 mg resveratrol, and in a range of 2 mg to 300 mg saffron powder. Most optionally, each dose is a daily dose of the composition which includes substantially 100 mg resveratrol and substantially 20 mg saffron powder.

Optionally, in respect of the composition, the saffron has a crocin content of at least 0.1%, more preferably at least 1%, and most preferably at least 10%.

Optionally, in respect of the composition, the resveratrol and the saffron are arranged to be consumed temporally concurrently.

Optionally, the composition additionally includes one or more of: lutein, zeaxanthin, vitamin C, vitamin E, vitamin D, fish oil comprising omega-3 fatty acids, Zinc, Copper, botanical extracts, N-acetyl-cysteine, coenzyme Q10 (either in form of ubiquinol or ubiquinone), L-carnitine and its derivatives, alpha-lipoic acid, and phytochemicals. These additional ingredients are susceptible to further support beneficial effects provided by the synergistic combination of resveratrol and saffron.

Moreover, these additional ingredients, among other mechanisms, are capable of functioning as antioxidants, sustaining cell energy production, and also improving cell membrane functionality.

Optionally, the composition includes vitamin C provided in a form of ascorbic acid.

Optionally, the composition includes vitamin E in a form of di-alpha tocopheryl acetate.

Optionally, the composition includes vitamin A is provided in a form of a retinly ester such as retinyl plamitate and/or retinyl acetate.

Optionally, the composition includes Zinc provided in a form of Zinc oxide, Zinc gluconate, or a combination thereof.

Optionally, the composition includes Copper provided in a form of Cupric oxide, Copper gluconate, Copper citrate, Copper bisglycinate, or a combination thereof.

Optionally, the composition includes a quantity of Lutein and Zeaxanthin, supplied as an herbal extract, or as a purified compound. More optionally, the Lutein and Zeaxanthin are supplied as Marigold extract (*Tagetes erecta*) (FLORAGLO™ or OPTISHARP™), or as a purified compound, Optionally, for convenient consumption, the composition is provided in liquid-form, in powder-form, in capsule-form and/or in tablet-form.

According to a second aspect of the invention, there is provided a pack including a plurality of tablets and/or capsules including a composition pursuant to the first aspect of the invention, wherein the pack includes said tablets and/or capsules disposed in manner together with graphical markings to assist users to consume a recommended dose of the composition over a period of duration extending over a plurality of days.

According to a third aspect of the invention, there is provided a method of manufacturing a composition pursuant to the first aspect of the invention, wherein the composition is prepared in powder-form, in capsular-form and/or in tablet form, wherein the method includes:

(a) obtaining resveratrol and saffron and subjecting these to at least one of drying, crushing, mixing, blending operations;

(b) preparing quantities of the composition in a form of powder, capsules and/or tablets; and (c) packaging the powder, capsules and/or tablets into packaging.

Optionally, the method includes adding edible carrier for providing bulk to the composition in step (a) of said method.

Optionally, the method includes providing a graphical arrangement in association with the packaging for advising a suitable daily dose of the powder, capsules and/or tablets.

Optionally, the method is implemented so that the composition is prepared to a dose pursuant to the first aspect of the invention.

According to a fourth aspect of the invention, there is provided a method of treating, ameliorating, preventing and/or decelerating development or progression of Age-related Macular Degeneration (AMD) and other age-related diseases, wherein the method includes administering to an individual a dietary nutritional composition comprising a composition pursuant to the first aspect of the invention.

Optionally, the composition for improving health is implemented such that each dose of the composition includes in a range of 1 mg to 10000 mg resveratrol, and in a range of 0.2 mg to 2000 mg saffron powder.

It will be appreciated that features of the invention are susceptible to being combined in various combinations without departing from the scope of the invention as defined by the appended claims.

DESCRIPTION OF THE DIAGRAMS

Figure 2:
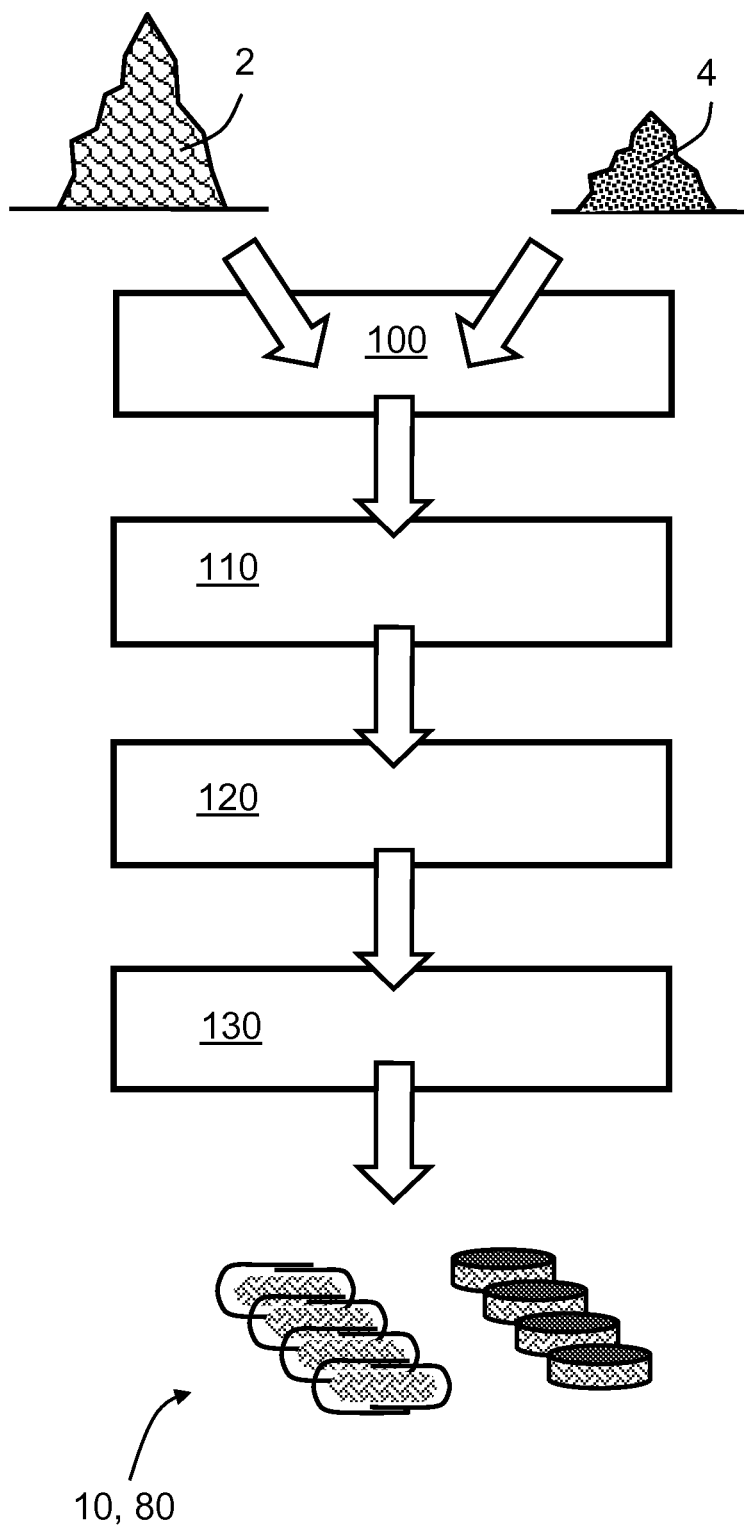
Figure 3:
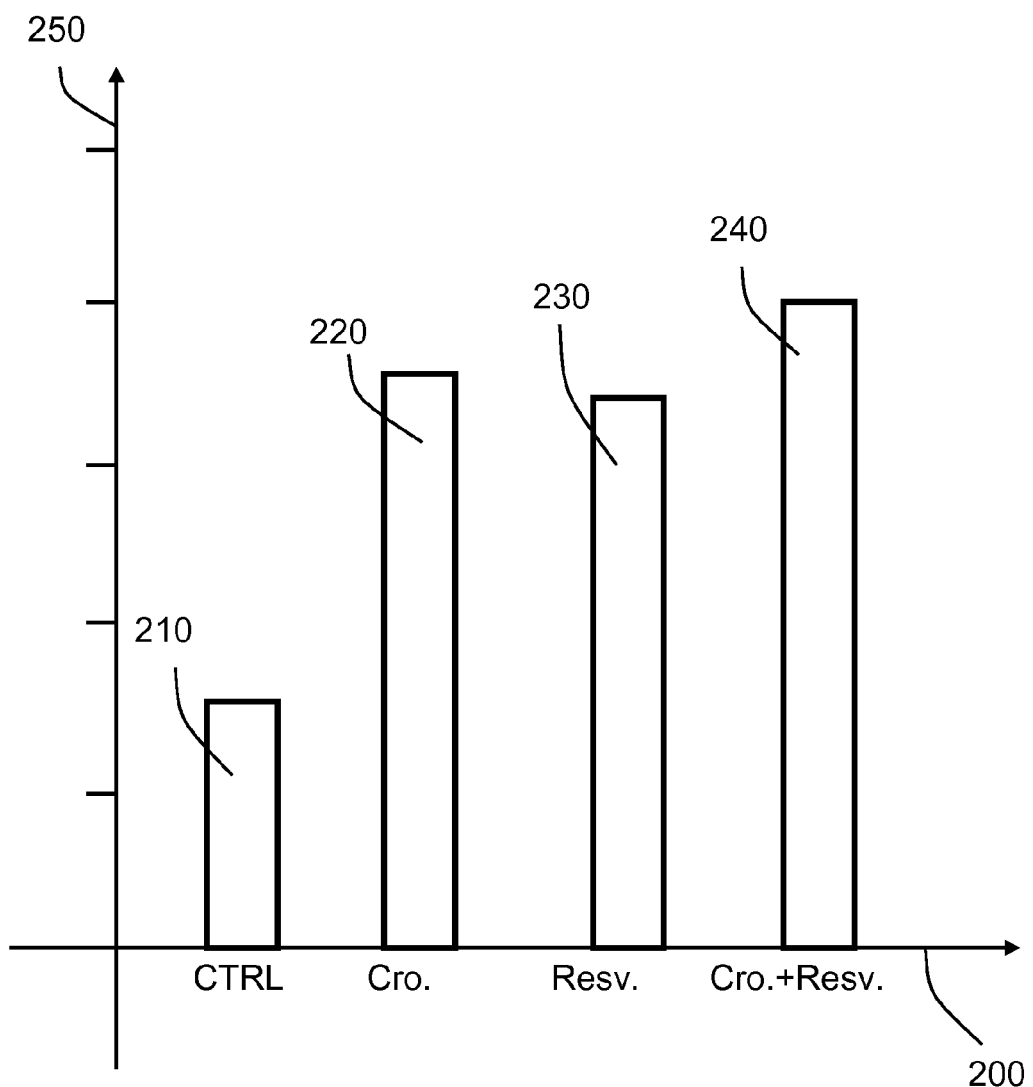

Embodiments of the present invention will now be described, by way of example only, with reference to the following diagrams wherein:

FIG. 1 is an illustration of a composition, for example a dietary supplement, pursuant to the present invention implemented as a capsule, a plurality of capsules, a tablet, a plurality of tables; and FIG. 2 is an illustration of steps of a method of manufacturing and implementing the composition of FIG. 1 in capsule and/or tablet form; and FIG. 3 is a graph illustrating synergistic benefits of employing a combination of crocin and resveratrol in association with experimental cell cultures including retinal cells (RPE).

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE INVENTION

Growing scientific evidence indicates that the pathology of onset of AMD is multi-factorial including: damage caused by free radicals, oxidative stress, photo-oxidative damage, and inflammation. In consequence, it is conventional intuitive reasoning to expect that treatment of AMD is unlikely to be treatable with merely administering a single medicinal solution. Surprisingly, the present invention concerns a synergistic combination of saffron and resveratrol substances which is indeed capable simultaneously of addressing several of these disparate causes of AMD. During development of the present invention, the inventors have appreciated that combining ingredients that posses multiple beneficial pharmacological effects via multiple targets is highly advantageous; such targets include cell-protective, anti-oxidative and gene modulation properties providing synergistic benefits.

From studies undertaken by the inventors of the present invention, resveratrol has shown to exert its protective effects on retinal cell by modifying multiple targets. It ameliorates symptoms of, and tendency to develop, AMD by inhibiting effects of damaging factors such as caspases, VEGF, and retinal activator protein-1, and by enhancing protective effects of factors as catalase, heme oxygenase-1, superoxide dismutase (Zheng et al., 2010), and sirtuin-1 (Kubota et al., 2010).

In juxtaposition to resveratrol, saffron has been found by the inventors to modify expression of completely different sets of genes in the retina of the human eye whose functions are deduced to be for protecting the retina from photo-oxidative damage, for reducing inflammation and for maintaining and restoring cellular function and structure.

The present invention is concerned with dietary supplements which are capable of temporally slowing development and/or progression of macular degeneration in human beings afflicted by loss of sight abilities. The dietary supplements are based upon a synergistically beneficial combination of saffron and resveratrol, wherein the combination is capable of providing enhanced benefits in comparison to a benefit provided when only one of saffron and resveratrol is administered to a human individual. One or more additional components are beneficially added to the aforementioned combination of saffron and resveratrol for providing further therapeutic benefits to the combination.

From experimental studies undertaken by the inventors of the present invention, statistical analysis of experimental data has shown that protective effects to functional retinal cells is achieved by applying a combination of resveratrol and crocin, wherein crocin is a significant component present in saffron. Moreover, the analysis clearly demonstrates a synergistic effect obtained from utilizing a combination of crocin and resveratrol in reducing damaging effects of light to RPE cells, namely a known cell-based model for AMD studies. Additionally, investigations in respect of toxicity of the combination to cells have shown no detrimental effects whatsoever, indicating that the combination is well tolerated by living tissue, for example functional retinal cells. In a similar manner to other dietary supplements, products embodying the present invention can be highly beneficial to health as a dietary supplement, both for AMD avoidance but also in respect of other beneficial metabolic effects.

Saffron

Saffron is a plant material obtained, for example, from bulbs of saffron crocuses (*Crocus sativus*) and/or their flowers, stigma or leaves. Saffron is conventionally used as a spice and also as a colouring material for food. Chemical analysis of saffron has identified that it includes antioxidant carotenoids such as crocin and crocetin.

When traditional medicines were earlier practiced, saffron was used as a treatment for conditions such as cancerous tumours and depression. Moreover, it was also known to exhibit an antioxidant effect when consumed by human individuals. Saffron has been found to protect human eyes from damaging effects of bright light and has shown a beneficial effect in human individuals suffering from early age-related macular degeneration (AMD). Results from a recent study indicated that orally consuming 20 mg/day of saffron for three months may induce a short-term and significant improvement of retinal function in early stages of AMD. However, as reported by Falsini et al., 2010, beneficial effects provided by saffron disappear after cessation of consumption of saffron-containing pills. Oral consumption of saffron may also be effective in slowing a progression of genetic diseases such as retinitis pigmentosa and Stargardt's Disease. Significantly, saffron provides benefit in respect of AMD, namely more benefits than would be expected based solely on antioxidant properties of its carotenoids; in other words, saffron or its components act through hitherto unknown one or more mechanisms of action which provide enhanced benefits. It appears that saffron potentially increases functional properties of human vision cells by affecting genes that regulate fatty acid metabolism. Moreover, saffron may protect human eye photoreceptors from retinal stress, and is believed to act as a regulator of apoptosis as reported by Maccarone et al., 2008 (Maccarone R, Di Marci S, Bisti S, 2008, "Saffron supplement maintains morphology and function after exposure to damaging light in mammalian retina", Invest Ophthalmol Vis Sci 49(3): pp. 1254-1261); Natoli et al., 2010 and Falsini et al., 2010.

It is believed that the carotenoid crocin exhibits a protective effect against blue light-and white light-induced rod and cone death in bovine and primate retinal cell cultures. For example, in a presence of 160 μM crocin, more than 90% of photoreceptors survived an effect of light exposure as reported by Laabich et al., 2006 (Laabich A, Vissvesvaran G P, Lieu K L, Murata K, McGinn T E, Manmoto C C, Sinclair J R, Karliga I, Leung D W, Fawzi A, Kubota R, 2006, "Protective effect of crocin against blue light- and white light-mediated photoreceptor cell death in bovine and primate retinal primary cell culture", Invest Ophthalmol Vis Sci 47(7): pp. 3156-3163).

Resveratrol

Resveratrol has a chemical composition 3,5,4″-trihydroxystilbene. Moreover, resveratrol is a natural polyphenolic phytochemical which exhibits upon oral consumption a variety of health effects for preventing age-related diseases and aging as reported by Valenzano et al., 2006 (Valenzano D R, Terzibasi E, Genade T, Cattaneo A, Domenici L, Cellerino A, 2006, "Resveratrol prolongs lifespan and retards the onset of age-related markers in a short-lived vertebrate", Curr Biol 6(3): pp. 296-300) and Lagouge et al., 2006 (Lagouge M, Argmann C, Gerhart-Hines Z, Maziana H, Lerin C, Daussin F, Massadeq N, Milne J, Lambert P, Elliot P, Laasko M, Puigserver P, Auwerx J, 2006, "Resveratrol improves mitochondrial function and protects against metabolic disease by activating SIRT1 and PGC-1alpha", Cell 127(6): pp. 1109-1122). Resveratrol is found in at least seventy two plant species and exists in two structural isomeric form, cis and trans; the trans form is more common of the two forms and also exhibits greater biological activity. Japanese giant knotweed plant (*Polygonum cuspidatum*) is a weed used in traditional Chinese and Japanese medicines and is also amongst richest sources of resveratrol. Primary dietary sources of resveratrol for human consumption include peanuts, peanut butter, grapes and red wine.

Resveratrol exhibits a diverse range of biological properties including antioxidant functionality, cardioprotection, anticancer activity, ant-inflammatory effects, estrogenic/anti-estrogenic properties, and modulation of cellular signal transduction pathways. It is believed that a polyphenolic structure confers to resveratrol its antioxidant activity; polyphenols are known for providing protection against oxidative stress, degenerative diseases, and aging processes as reported by Zheng et al., 2010. A comprehensive review regarding biological activities of resveratrol has been provided by Queen and Tollefsbol, 2010 (Queen B L, Tollefsbol T O, 2010, "Polyphenols and aging", Curr Aging Sci 3(1): pp 34-42), by Lavu et al., 2008 (Lavu S, Boss O, Elliott P J, Lambert P D, 2008, "Sirtuins—novel therapeutic targets to treat age-associated diseases", Nat Rev Drug Discov 8(10): pp. 841-853), and also King et al., 2006. The antioxidant and anti-aging properties of resveratrol arise through activation of a SIRT1 human gene and by mimicking calorie-restriction conditions as reported by Smith et al., 2009 (Smith J J, Kenney R D, Gagne D J et al., 2009, "Small molecule activators of SIRT1 replicate signalling pathways triggered by calorie restriction in vivo", BMC Syst Biol 3:31), by Kim and Um, 2008 (Kim E J, Um S J, 2008, "SIRT1: roles in aging and cancer", BMB Rep. 41(11): pp. 751-756), by Pillarisetti, 2008, and also Elliot and Jirousek, 2008 (Elliot P J, Jirousek M, 2008, "Sirtuins novel targets for metabolic diseases", Curr Opin Investig Drugs 9(4): pp. 371-378).

Presently, an exact pathogenesis of AMD is not clear, although growing scientific evidence suggests a role for retinal pigment epithelial (RPE) cell damage and death caused by oxidative stress, and possibly inflammation. A human retina is particularly susceptible to oxidative damage on account of its high consumption of oxygen and also its frequent exposure to light. Dietary supplements with antioxidant properties have demonstrated effectiveness in preventing a progression to advanced AMD, as reported by Kubota et al., 2009 (Kubota S, Kurihara T, Mochimaru H, Satofuka S, Noda K, Ozawa Y, Olike Y, Ishida S, Tsubota K, 2009, "Prevention of ocular inflammation in endotoxin-induced uveitis with resveratrol by inhibiting oxidative damage and nuclear factor-kappaB activation", Invest Ophthalmol Vis Sci 50(7): pp. 3512-3519) and also Chucair et al., 2007 (Chucair A J, Rotstein N P, Sangiovanni J P, During A, Chew E Y, Politi L E, 2007, "Lutein and zeaxanthin protect photoreceptors from apoptosis induced by oxidative stress: relation with docosahexaenoic acid", Invest Ophthalmol Vis Sci 48(11): pp. 5168-5177).

An Age-Related Eye Disease Study (AREDS) has been undertaken whose results have indicated that supplementation with both antioxidant vitamins and Zinc is potentially capable of preventing development of most advanced stages of AMD. In the AREDS study, 500 mg of vitamin C, 400 International Units (IU) of vitamin E, 15 mg of beta-carotene, 80 mg of Zinc in a form of Zinc Oxide in combination with 2 mg Copper in a form of Cupric Oxide were administered daily to participants of AREDS. The participants were divided into four separate treatment groups: a first group was administered anti-oxidants alone, a second group was administered Zinc alone, a third group was administered anti-oxidants and Zinc, and a fourth group was a control with no treatment being provided. The AREDS revealed that a combination of Zinc and antioxidants provided an effective treatment for preventing development of late stage AMD as reported by Sangiovanni et al., 2009 (Sangiovanni J P, Chew E Y, Clemons T E, Davis M D, Ferris F L $3^{rd}$, Genser G R, Kurinij N, Lindblad A S, Milton R C, Seddon J M, Sperduto R D, 2007, "The relationship of dietary lipid intake and age-related macular degeneration in a case-control study: AREDS Report No. 20, Arch Ophthalmo 125(5): pp. 671-679). Based on interpretation of results from AREDS1 study, recommendations have been to start taking a combination of antioxidants plus Zinc (AREDS formulation) by people at high risk for developing advanced AMD, including individuals either with intermediate AMD in one or both eyes, or with advanced AMD in one eye, but not the other eye.

From studies, it is found that retinal pigment epithelial (RPE) lipofuscin is a morphologic marker of cellular aging, and has been used to evaluate age- and disease-related pathophysiological changes in human retina. For example, in a case of an eighty year old man with complaints of unremitting night driving difficulties and parafoveal deposition of retinal lipofuscin, visible clearing of RPE lipofuscin was observed by using a daily oral polyphenolic mixture, LONGEVINEX™, containing 100 mg resveratrol per capsule for 5 months; Moreover, clinically measurable and subjective improvements in vision, including self-reported night vision, dramatic improvement in contrast sensitivity function and mental function were achieved as reported by Richer et al., 2009 (Richer S, Stiles W, Thomas C, 2009, "Molecular medicine in ophthalmic care", Optometry 80(12): pp. 695-701).

A contemporary aforementioned product for use in treating AMD is LONGEVINEX™ (Resveratrol partners LLC) which contains as active ingredients per capsule:

(i) 5 mg vitamin E as mixed tocopherols;

(ii) 215 mg total resveratrol, obtained from French red wine and giant knotwood (*Polygonum cuspidatum*), providing 100 mg of resveratrol;

(iii) 25 mg quercetin dihydrate;

(iv) 75 mg physic acid, namely rice bran extract;

(v) 380 mg rice bran oil; and (vi) 55 mg sunflower lecithin, as described in US patent application no. 2009/0169585.

It is known that abnormal angiogenesis is central to the pathophysiology of visually debilitating eye diseases such as AMD. Abnormal angiogenesis is potentially susceptible to affect the human choroid, as found in choroidal neovascularisation (CNV) and potentially may lead to blindness. Resveratrol in both in vitro and in vivo experiments performed in mouse retina was found to inhibit pathological angiogenesis by a sirtuin-independent pathway. Moreover, it was found that resveratrol also exhibited properties of inhibiting proliferation and migration of vascular endothelial cells, as reported by Khan et al., 2010 (Khan A A, Dace D S, Ryazanov A G, Kelly J, Apte R S, 2010, "Resveratrol regulates pathologic angiogenesis by a eukaryotic elongation factor-2 kinase-regulated pathway", Am J Pathol 177 (1): pp. 481-492).

Resveratrol has also exhibited protective benefits in respect of retina via modulation of nitric oxide synthase in in vitro and in vivo oxygen-induced retinopathy models as reported by Kim and Suh, 2010 (Kim W T, Suh E S, 2010: "Retinal protective effects of resveratrol via modulation of nitric oxide synthase on oxygen-induced retinopathy", Korean J Ophthalmol 24(2): pp. 108-118). Moreover, resveratrol has also shown potential for ameliorating age-related RPE degeneration, for example AMD; resveratrol has been implicated through its protective effects on acrolein-induced oxidative stress in human RPE cells as reported by Sheu et al., 2010 (Sheu S J, Liu N C, Chen J L, 2010 "Resveratrol protects human retinal pigment epithelial cells from acrolein-induced damage", J Ocul Pharmacol Ther 26(3): pp. 231-236). Furthermore, it is also known that light damage to retina accelerates retinal degeneration, and that oral consumption of resveratrol in mice is capable of preventing retinal degradation related to such light damage, as reported by Kubota et al., 2010 (Kubota S, Kurihara T, Mochimaru H, Satofuka S, Noda K, Ozawa Y, Olike Y, Ishida S, Tsubota K, 2009: "Prevention of ocular inflammation in endotoxin-induced uveitis with resveratrol by inhibiting oxidative damage and nuclear factor-kappaB activation", Invest Ophthalmol Vis Sci 50(7): pp. 2512-3519). Thus, oral consumption of resveratrol supplements is believed to offer a potential for modulating risks associated with development and progression of AMD. However, the present invention is concerned with greatly enhanced benefits from resveratrol by co-administering saffron. As aforementioned, co-administration of resveratrol and Zinc is known, but the present invention adopts an alternative approach in comparison to contemporary practice.

Omega-3 Fatty Acids

Emerging evidence suggests that omega-3 fatty acid, namely long-chain polyunsaturated fatty acids (LCPUFAs) and fish intake may potentially reduce a likelihood of disease progression in patient with advanced AMD, as reported by Sangiovanni et al., 2007 (Sangiovanni J P, Chew E Y, Clemons T, Davis M D, Ferris F L 3$^{rd}$, Gensler G R, Kurinij N, Lindblad A S, Milton R C, Seddon J M, Sperduto R D, 2007, "The relationship of dietary lipid intake and age-related macular degeneration in a case-control study: AREDS Report No. 20, Arch Ophthalmo 125(5): pp. 671-679), by Sangiovanni et al., 2008 (Sangiovanni J P, Chew E Y, Agrón E, Clemons T E, Ferris F L 3$^{rd}$, Gensler G, Lindblad A S, Milton R C, Seddon J M, Klein R, Sperduto R D, 2008, "The relationship of dietary omega-3 long-chain polyunsaturated fatty acid intake with incident age-related macular degeneration: AREDS Report No. 23, Arch Ophthalmo 126(9): pp. 1274-1279), by Augood et al., 2008 (Augood C, Chakravarthy U, Young I, Vioque J, de Jong P T, Bentham G, Rahu M, Seland J, Soubrane G, Tomazzoli L, Topouzis F, Veingerling J R, Fletcher A E, 2008, "Oily fish consumption, dietary docosahexaenoic acid and eicosapentaenoic acid intakes, and associations with neovascular age-related macular degeneration", Am J Clin Nutr 88(2): pp. 398-406), and by Chong et al., 2008 (Chong E W, Kreis T Y, Simpson J A, Guymer R H, 2008, "Dietary omega-3 fatty acid and fish intake in the primary prevention of age-related macular degeneration: a systematic review and meta-analysis", Arch Ophthalmol 126(6): pp. 826-833). Moreover, omega-3 fatty acids, namely docosahexaenoic acid (DHA) and eicosapentaenoic acid (EPA), have the capacity, particularly supplemented with antioxidants, to modulate processes implicated in AMD pathogenesis, as reported by Tan et al., 2009 (Tan J S, Wang J J, Flood V, Mitchell P, 2009, "Dietary fatty acids and the 10-year incidence of age-related macular degeneration: the Blue Mountains Eye Study", Arch Ophthalmol 127/5): pp. 656-665), by Tuo et al., 2009 (Tuo J, Ross F J, Herzlich A A, Shen D, Ding X, Zhou M, Coon S L, Hussein N, Salem N Jr, Chan C C, 2009, "A high omega-3 fatty acid diet reduces retinal lesions in a murine model of macular degeneration", Am J Pathol 175(2): pp. 799-807), and by Cangemi 2007. The positive effect of omega-3 fatty acids has been demonstrated in an Age-related Eye Disease Study (AREDS) in which participants to the study reported that a highest baseline consumption of omega-3 fatty acids were approximately 30% less likely than their peers reporting lowest omega-3 fatty acid consumption to develop advanced AMD, as reported by Chong et al., 2009 (Chong E Q, Robman L D, Simpson J A, Hodge A M, Aung K Z, Dolphin T K, English D R, Giles G G, Guymer R H, 2009, "Fat consumption and its association with age-related macular degeneration", Arch Ophthalmol 127(5): pp: 674-680), and by Sangiovanni et al., 2008 (Sangiovanni J P, Chew E Y, Agrön E, Clemons T E, Ferris F L 3$^{rd}$, Gensler G, Lindblad A S, Milton R C, Seddon J M, Klein R, Sperduto R D, 2008, "The relationship of dietary omega-3 long-chain polyunsaturated fatty acid intake with incident age-related macular degeneration: AREDS Report No. 23, Arch Ophthalmo 126(9): pp. 1274-1279). Thus, it is becoming appreciated that omega-3 fatty acid nutrients may potentially represent a straightforward approach to modify a risk of AMD progression. However, the present invention provides an innovation to merely employing omega-3 supplements by optionally employing omega-3 fatty acids in combination with saffron and resveratrol.

Lutein and Zeaxanthin

Lutein and zeaxanthin are macular carotenoids of dietary origin. As reported by Huang et al., 2008 (Huang L L, Coleman H R, Kim J, de Monasterio F, Wong W T, Schleicher R L, Ferris F L 3$^{rd}$, Chew E Y, 2008, "Oral supplementation of lutein/zeaxanthin and omega-3 long chain polyunsaturated fatty acids in persons aged 60 years or older, with or without AMD", Invest Ophthalmol Vis Sci 49(9): pp. 3864-3869), a dietary supplementation of lutein and/or zeaxanthin and in combination with omega-3 fatty acids is associated with a reduced risk of occurrence of advanced age-related macular degeneration (AMD). Moreover, improvements seen with lutein potentially arise on account of its protective role as a blue light filter and as an antioxidant, as reported by Johnson et al., 2008 (Johnson E J, Chung H Y, Caldarella S M, Snoddery D M, 2008, "The influence of supplemental lutein and docosahaenoic acid on serum, lipoproteins, and macular pigmentation", Am J Clin Nutr 87(5): pp. 1521-1529), by Chucair et al., 2007 (Chucair A J, Rotstein N P, Sangiovanni J P, During A, Chew E Y, Politi L E, 2007, "Lutein an zeaxanthin protect photoreceptors from apoptosis induced by oxidative stress: relation with docosahexaenoic acid", Invest Ophthalmol Vis Sci 48(11): pp. 5168-5177), and by Rotstein et al., 2003 (Rotstein N P, Politi L E, German O L, Girotti R, 2002, "Protective effect of docosahexaenoic acid on oxidative stress-induced apoptosis of retina photoreceptors", Invest Ophthalmol Vis Sci 2003, 44(5): pp. 2252-2259). Furthermore, supplements containing lutein, zeaxanthin and omega-3 fatty acids have been shown in cell cultures to promote photoreceptor survival and differentiation by exerting neuroprotection and antiapoptotic effect on retina photoreceptors; these effects are believed to arise on account of antioxidant properties and other mechanisms such as activation of intracellular signalling pathways. The effects have been identified by way of in vitro findings which support epidemiologic evidence that dietary supplements may act as factors that modulate processes implicated in AMD pathogenesis and progression, as reported by Chucair et al., 2007 (Chucair A J, Rotstein N P, Sangiovanni J P, During A, Chew E Y, Politi L E, 2007, "Lutein and zeaxanthin protect photoreceptors from apoptosis induced by oxidative stress: relation with docosahexaenoic acid", Invest Ophthalmol Vis Sci 48(11): pp. 5168-5177).

It has been found that an average dietary intake of greater than 6 mg/day of lutein is not uncommon in many human diets. However, on account of lutein competing with other carotenoids for absorption, it appears to be prudent to employ a maximum limit of 6 mg/day lutein in a dietary supplement, as reported by Jones, 2007 (Jones A A, 2007, "Age related macular degeneration—should your patients be taking additional supplements?", Aust Fam Physician 36(12): pp. 1026-1028), although such a limit is beneficially optionally exceeded.

In a clinical study AREDS2, depending on study group related to randomization, lutein has been used at a dose of 10 mg/day, zeaxanthin at 2 mg/day, DHA at 350 mg/day, EPA at 650 mg/day, vitamin C at 500 mg/day, vitamin E at 400 IU/day, beta-carotene at 15 mg/day, and Zinc Oxide at 25 mg/day or 80 mg/day, together with Cupric Oxide at 2 mg/day. Details of the study are viewable at an Internet website for areds2.org.

Despite numerous investigations and studies as elucidated in the foregoing, a clearly most beneficial dietary supplement for addressing AMD has not seemingly yet evolved, although certain combinations of resveratrol, omega-3 oils and mineral substances have provided some benefits in respect of reducing severity of AMD. In contradistinction, the present invention has an objective to take advantage of positive effects of a synergistic combination of saffron and resveratrol for providing a dietary composition which exhibits significant effects for reducing a risk of developing macular degeneration, for slowing down the progression of the disease once it has developed, and for preventing age-related sight loss and other age-related diseases. Moreover, the present invention also aims to provide a composition comprising quantities of resveratrol and saffron that can be added to dietary formulations arising from AREDS1 and AREDS2 studies, to improve further their eye health benefits in AMD, cataracts, and similar eye conditions. Furthermore, the present invention seeks to provide a composition, which, in addition to eye protection effect, is useful as an antioxidant and anti-aging formulation for other age-associated health conditions.

The inventor has appreciated that it is beneficial to regard AMD as temporally comprising three stages: early-AMD, intermediate-AMD and advanced-AMD. Saffron and resveratrol function to provide benefits at each of these three stages of AMD to improve vision, but saffron is most beneficial at the early-AMD phase, with a beneficial effect appearing in relatively short period of time after taking saffron supplementation, and resveratrol is highly beneficial, by way of gene modulation, to reduce vascularisation in advanced-AMD, and with health benefits in slowing the progression of intermediate AMD to advanced AMD.

It is thus grossly over simplistic merely to consider saffron and resveratrol as antioxidants and that their combination merely provides a summation of antioxidant effects; the present invention is far more complex in its manner of biological activity. The present invention makes use of a manner of biological action which is very different to earlier attempts to ameliorate AMD; resveratrol affects retinal sirtuin 1 (SIRT1) and retinal activator protein 1 and also provides retinal neuroprotective effects, whereas saffron modulates activity of genes such as chemokine (C-C motif) ligand 2 (cc/2), and noc-coding RNA sequences (nc-RNAs) as well as providing an antioxidative effect. Saffron via a combination of its antioxidative and gene modifying activities is effective for improving both retinal morphology and function, while treatment with the antioxidant beta-carotene is ineffective for maintaining retinal function, and only improved morphology (Maccarone R, Di Marco S, Bisti S, 2008, "Saffron supplement maintains morphology and function after exposure to damaging light in mammalian retina", Invest Ophthalmol Vis Sci 49(3): pp. 1254-1261).

The present invention relates to a dietary supplement comprising a combination of saffron and resveratrol. Such a combination is useful as a nutritional supplement, and anti-aging product, and an antioxidant. The saffron and resveratrol are optionally temporally coincidentally administered to individuals. Alternatively, the saffron and resveratrol are administered with a time difference therebetween. Beneficially, the time difference is less than 6 hours, and preferably less than 2 hours. Optionally, the combination is administered in a mutually blended state. Alternatively, the saffron and resveratrol are administered as separate doses.

The present invention also provides a method of treating, ameliorating or decreasing a temporal rate of development of age-related macular degeneration and other degenerative conditions by administering a dietary supplement, wherein the dietary supplement includes a combination of saffron and resveratrol, for example by administered saffron and resveratrol temporally concurrently or with a time interval therebetween.

Although a synergistic combination of saffron and resveratrol provides principal benefits in respect of the present invention, it is optionally beneficial to supplement the combination with one or more ingredients selected from: omega-3 fatty acids, Zinc, Copper, vitamin E, vitamin C, antioxidant leutein, N-acetyl-cysteine, coenzyme Q10, L-carnitine and its derivatives, alpha-lipoic acid, and antioxidant zeaxanthin. These optional one or more ingredients are functional as antioxidants, gene regulators, cell membrane components and cell function modifiers. It is through such mechanisms that these one or more ingredients exhibit their protective benefits in respect of ameliorating AMD and also beneficial effects in age-related diseases in general.

Optionally, in a preferred embodiment of the present invention, there is provided a dietary supplement comprising in a range of 1 mg to 10000 mg resveratrol in combination with in a range of 0.2 mg to 2000 mg saffron, for example in a form of saffron powder. More optionally, in a preferred embodiment of the present invention, there is provided a dietary supplement comprising in a range of 5 mg to 5000 mg resveratrol in combination with in a range of 1 mg to 1000 mg saffron, for example saffron powder. More optionally, in a preferred embodiment of the present invention, there is provided a dietary supplement comprising in a range of 50 mg to 700 mg resveratrol in combination with in a range of 2 mg to 300 mg saffron, for example saffron powder. Most preferably, in a preferred embodiment of the present invention, there is provided a dietary supplement comprising substantially 100 mg resveratrol in combination with substantially 20 mg saffron; the saffron is beneficially provided as saffron powder, for example prepared from saffron stigmas.

Referring to FIG. 1, the aforementioned combination 6 of at least resveratrol 2 and saffron 4 is beneficially provided in a form of one or more capsules 10. Each capsule 10 beneficially has an outer coating of gelatine 20, for example a complete layer of gelatine or two gelatine components 30A, 30B that are operable mutually to engage to define an internal volume for retaining a quantity 40 of the combination of resveratrol 2 and saffron 4. The gelatine 20 is optionally substituted by cellulose derivatives for vegetarian versions of the one or more capsules 10. The gelatine 20 is beneficially broken down within human intestines to allow absorption of the quantity 40 of the combination 6 of resveratrol and saffron. The quantity 40 is beneficially provided within the capsule 10 by way of a carrying material; optionally, the carrying material includes one or more of: Magnesium stearate, Silicon dioxide, an organic dried digestible material, edible colouring materials, flavourings, one or more edible binding agents such a plant gum. Optionally, the resveratrol 2 and saffron 4 components are included in mutually separate capsules 10 which are consumed by users temporally coincidentally or with a time difference therebetween. Optionally, the resveratrol 2 and saffron 4 components are included mixed within the one or more capsules 10. Alternatively, the resveratrol 2 and saffron 4 combination is provided in a compacted form as one or more tablets 80, either separately or combined in a similar manner as for the capsules 10. Beneficially, the one or more capsules 10 and/or the one or more tablets 80 are provided in a pack, for example a hermetically-sealed blister pack which is often employed for contemporary medicines and dietary supplements. Optionally, the pack is provided with visual indications, for example a calendar-type marking adjacent to the capsules 10 or tablets 80, to indicate to users whether or not the capsules 10 or tablets 80 have been consumed. Such markings are especially beneficial to elderly users whose cognitive abilities may be slightly impaired or confused and who could risk consuming an overdose of the capsules 10 or tablets 80.

In FIG. 2, there is shown in outline steps of a process for manufacturing packs of capsules 10 and/or tablets 80 including a synergistic combination of resveratrol 2 and saffron 4 pursuant to the present invention. The process includes a first step 100 of procuring resveratrol 2 and saffron 4 ingredients, a second step 110 of adding the resveratrol 2 and/or saffron 4 to a suitable edible carrier to generate a working material, a third step 120 of forming the working material into a capsular form and/or tablet form, and a fourth step 130 of packaging the capsules and/or tablets into packs.

In the first step 100, resveratrol is commercially available, for example under a trade name PROTYKIN™ from Inter-Health Nutraceuticals Inc. of Beencia, Calif. or from Linyi Taihao International Trade Co. Ltd., Shandong, China. Saffron is commercially available from a plurality of wholesale suppliers, for example saffronspices.co,uk or irandriedfruit. com. Synthetic resveratrol is available, namely RESVIDA™, and is optionally produced using fermentation processes.

In the second step 110, the resveratrol 2 and saffron 4 are suitably diluted or otherwise dispersed within a carrier material to generate the working material. Operations such as drying, grinding, blending and mixing are employed in the second step 110, for example by using suitable grinding apparatus.

In the third step 120, the working material is formed into the one or more capsules 10 and/or the one or more tablets 80, for example by employing standard pharmaceutical-type capsule or tablet manufacturing apparatus, for example as described in a published patent application no. EP 0667147A2, Fuisz Technologies Ltd., "Process and apparatus for making tablets and tablets made therefrom", which is hereby incorporated by reference.

In the fourth step 130, the capsules 10 and/or tablets 80 are packaged into sheets or packed into bottles, for example 20-day or 30-day consumption, optionally with hermetic sealing being provided for the capsules 10 and/or tablets 80, wherein the sheets are optionally marked with graphical features which assist users to ensure correct daily dosage, and optionally a plurality of such sheets are packaged into cardboard or plastic boxes ready for sale to users.

Optionally, pharmaceutically-acceptable dosage forms for administration of the aforementioned composition 6 including resveratrol 2 and saffron 4 includes one or more of the following: tablets, capsules, powder, paste, solutions, suspensions, gels. Preferably, as aforementioned, tablets and/or capsules are beneficially used for oral administration of dietary supplements pursuant to the present invention.

Beneficially, administration of dietary supplements, for compositions, pursuant to the present invention is undertaken whenever AMD is diagnosed. Alternatively, or additionally, administration of dietary supplements, for example compositions, pursuant to the present invention is undertaken for preventing development of AMD and/or other age-related diseases.

Resveratrol exhibits its benefits in ameliorating symptoms of, and tendency to develop, AMD by inhibiting the effect of damaging factors such as caspases and retinal activator protein-1, and by enhancing the protective effect of factors such as catalase, heme oxygenase-1, superoxide dismutase (Zheng et al, 2010), and sirtuin-1 (Kubota et al., 2010).

A wide range of possible retinal protective mechanisms is also suggested for saffron 4 which has been shown to regulate the expression of many retinal genes and non-coding RNA sequences. The effect of saffron includes direct regulatory effect on tissue oxidative protection, reduction of inflammation due to the down regulation of chemokine (C-C motif) ligand 2 (ccl2), which has been shown to play a role in the development of retinal degeneration, and particularly down regulation of many non-coding RNAs (nc-RNAs), whose protective role need further investigation (Natoli et al., 2010).

Therefore, it will be understood that the protective effects of both resveratrol 2 and saffron 4 are more than that of a direct antioxidant property; rather, saffron and resveratrol appear to interact very significantly with different intracellular/signalling pathways and modify gene expression levels, for example to different extents at various temporal stages in the development and progression of AMD. Given the number of retinal genes/entities involved and regulated by resveratrol and saffron, along with preclinical data and somewhat limited clinical results, a synergistic ocular effect occurs by using a combination of resveratrol with saffron, for example in a single nutritional supplement.

It is further anticipated that the synergistic eye health benefits of resveratrol 2 and saffron 4 in combination will be further enhanced by adding one or more of: antioxidant vitamins C and E, zinc, vitamin A, and the macular pigments lutein and zeaxanthin, fish oils or plant-derived oils including omega-3 fatty acids to the combination, individually, in different combinational permutations thereof, or all ingredients together in one supplementary dietary product.

On account of saffron and resveratrol each showing positive effects in a plurality of other age-associated diseases (Bathaeie and Mousavi, 2010; Queen & Tollefsbol, 2010; Lavu et al., 2008; King et al., 2006), the product of this invention and variations thereof, can be effective in diseases such as depression, Alzheimer's disease, Parkinson's disease, metabolic diseases, digestive disorders, insulin resistance and type 2 diabetes, cardiovascular diseases, atherosclerosis, cancer, obesity and inflammatory diseases.

In relation to description of the present invention in the foregoing, it is beneficial that Lutein is obtained, for example, as FLORAGLO™ extract. Either Lutein or Zeaxanthin may be prepared by chemical synthesis. Saffron in a form of a suitable powder is a traditional spice, and is prepared from stigma (namely filaments) and/or stigma plus style of saffron flower (*Crocus sativus* L.). It is feasible to obtain main active ingredients found in saffron from other plants such as *Yucca perculosa, Gardenia Jasminoides*, or *Camelia sinensis*.

For purposes of preparing products and compositions pursuant to the present invention, either saffron powder, or a suitable extract prepared from saffron, purified active compounds, or derivatives thereof, alone or in combination may be used; such extract beneficially includes one or more of: crocin, crocetin, picrocrocin. For example, pure crocin with resveratrol may be employed pursuant to the present invention in order to achieve synergistic eye health benefits. Crocin and other active components of saffron may be obtained either by extraction and purification from saffron plants (*Crocus sativus*), other plants, or may be prepared by chemical synthesis. Additionally, the active ingredients of saffron may be obtained from capejasmine fruit instead of saffron at a lower cost as described in a Chinese patent no. CN1123663 (A) which has a publication date 5 Jun. 1996. Analogs of active compounds crocin, crocetin and/or safranal, crocin monglycoside, diglucosides, or mixture thereof are optionally prepared for implementing the present invention by following methods described in a US patent application no. 2010/0210572. Optionally, other analogs of crocin or crocetin, with similar biological activities such as amides, esters, thioesters or other derivatives are susceptible to being prepared by those skilled in the art. Optionally, contents found in naturally grown saffron, namely safranal, crocetin, crocin or their analogs are prepared by culturing saffron stigma in an artificial culture base containing cytokinin as described in Japanese patent application no. JP63109788 (A). Optionally, crocin glucoside is obtained by synthetic routes for cost saving and scale-up issues as described in a Chinese patent no. CN101514216 (A) which has a publication date of 26 Aug. 2009.

Resveratrol is provided from a suitable plant extract containing a sufficient quantity of resveratrol, particularly in the form of trans-isomer, or produced by microbial fermentation, or made through synthetic routes such as RESVIDA™ (DSM). The plant Japanese giant knotweed (*Polygonum cuspidatum*) is a well known and represents a commercial source of resveratrol. Resveratrol is found in various plants, including grapes, peanuts, mulberries, berries and peanuts and *Veratrum grandiflorum O. Loes*. For the purpose of this invention either resveratrol or a suitable chemical derivative or analogue of resveratrol such as pterostilbene, or a composition thereof, are optionally employed which possess similar biochemical/gene modifying properties, and exhibit similar eye health benefits. Pterostilbene is beneficially obtained from various plants including *Pterocarpus marsupium*.

Such formulations may be constructed in a dosage formulation for human consumption. Administering such formulations may include one or more of the functions of administering a solid formulation, injecting the formulation, or administering the formulation on human skin, or administering the formulation orally in a liquid form, or the formulation may be manufactured in other dosage forms known to those skilled in the art. The formulation of this invention may be considered for adding to food. The fortified foods will present alternative sources of the ingredients.

For oral administration, the compositions of the invention can take the form of, for example, liquid portions, tablets including effervescent tablets, capsules, or lozenges prepared by conventional means with acceptable excipients such as binding agents, fillers, lubricants, disintegrants, or wetting agents. The tablets are optionally coated by methods well known in the art, for example with sugars, films or enteric coatings.

Preparations pursuant to the present invention for oral administration are beneficially suitably formulated to give controlled release of the composition, namely over an extended period of time as is known for other types of medications.

For buccal administration, the compositions pursuant to the present invention beneficially take the form of tablets or lozenges formulated in conventional manner.

Liquid preparations for oral administration pursuant to the present invention are beneficially prepared, for example, in the form of elixirs, solutions, syrups or suspensions, or they are beneficially presented as a dry product for constitution with water, beverages, yogurt or other suitable vehicle before use. Such liquid preparations are beneficially prepared by conventional means with acceptable additives such as suspending agents, non-aqueous vehicles, and preservatives. The preparations beneficially also include buffer salts, flavouring, colouring, sweetening, and acidity controlling agents as appropriate.

Alternatively, other delivery systems are beneficially employed, such as preparation into soft gelatin or cellulose-based capsules or those formulations prepared by nanotechnology, such as nano-dispersion, nano-emulsion or nano-encapsulation.

In order to achieve optimal health benefits tailored to each individual's genetic background, a method of implementing the present invention includes measuring beneficial health effects of the product or composition by applying technologies in nutrigenomics, and subsequently using the information, for example, to adjust the composition of the formulation, or the number of servings per day.

EXAMPLES

The following formulations (Tables 1 to 4) are merely non-exhaustive illustrative examples of the present invention.

1 Tablet:

TABLE 1

| Ingredient | Dose in mg |
|---|---|
| Microcrystalline cellulose | 70 |
| Saffron stigma powder | 20 |

TABLE 1-continued

| Ingredient | Dose in mg |
|---|---|
| trans-Resveratrol | 100 |
| Potato maltodextrin | 50 |
| Potato starch | 5 |
| Magnesium stearate (anti-agglomerate) | 5 |
| Colloidal silica (fluidizing agent) | 5 |
| TOTAL | 255 |

2) Tablet including vitamins, minerals, lutein/zeaxanthin

TABLE 2

| Ingredient | Dose in mg |
|---|---|
| Vitamin C | 150 |
| Vitamin E | 85 |
| Zinc | 25 |
| Copper | 2 |
| Lutein | 10 |
| Zeaxanthin | 2 |
| Saffron stigma powder | 20 |
| trans-Resveratrol | 100 |
| Vitamin A | 0.8 |
| Potato starch | 5 |
| Magnesium stearate (anti-agglomerate) | 5 |
| Colloidal silica (fluidizing agent) | 5 |
| TOTAL | 409.8 |

Optionally, the tablets may be covered by a film coating blend.

3) Capsule

TABLE 3

| Ingredient | Dose in mg |
|---|---|
| Vitamin C | 150 |
| Vitamin E | 85 |
| Zinc | 10 |
| Copper | 1 |
| Lutein | 10 |
| Zeaxanthin | 2 |
| Saffron stigma powder | 20 |
| trans-Resveratrol | 100 |
| Vitamin A | 0.8 |
| Riboflavin (vitamin B2) | 1.4 |
| Magnesium stearate (anti-agglomerate) | 5 |
| Colloidal silica (fluidizing agent) | 5 |
| TOTAL | 390.2 |

4) Dual-pack product; capsule and softgel

TABLE 4

| Ingredient | Dose in mg |
|---|---|
| CAPSULE: | |
| Microcrystalline cellulose | 70 |
| Vitamin C | 150 |
| Vitamin E | 83 |
| Zinc | 10 |
| Copper | 1 |
| Saffron stigma powder | 20 |
| trans-Resveratrol | 100 |
| Vitamin A | 0.8 |
| Riboflavin (vitamin B2) | 1.4 |

TABLE 4-continued

| Ingredient | Dose in mg |
|---|---|
| Magnesium stearate (anti-agglomerate) | 5 |
| Colloidal silica (fluidizing agent) | 5 |
| TOTAL Capsule | 446.2 |
| SOFTGEL: | |
| Fish oil (EPA 10%/DHA 43.4%) | 577 |
| Vitamin E | 2 |
| Lutein | 10 |
| Zeaxanthin | 2 |
| TOTAL Softgel | 591 |

Although various ratios of ingredients resveratrol and saffron are described in the foregoing for manufacturing a composition pursuant to the present invention, it will be appreciated that examples of the present invention optionally have over ratios of these ingredients over a relatively broad range of ratios, for example weight ratios in a range of 1:0.01 to 1:0.5, preferable in a range of 1:001 to 1:1, and most preferably in a range of 1:0.0001 to 1:10.

Experimental tests executed by the inventors of the present invention have been, for example, undertaken in respect of a synergistic combination of crocin and resveratrol, wherein crocin is an important component of saffron, and is known for possessing eye health benefits, as aforementioned. For implementing the experimental tests, a method including the following steps is beneficially employed:

STEP 1: dissolving crocin and resveratrol in 100% dimethy sulfoxide (DMSO) and then subsequently further diluting with DMSO to provide a test composition;

STEP 2: preparing a cell culture medium and then adding the composition to investigate effects on the cell culture whilst the cell culture medium is exposed to optical radiation; and STEP 3: performing a post-radiation exposure analysis of the cell culture.

When implementing the method, concentrations of 10 $\mu$M to 500 $\mu$M crocin and 0.1 $\mu$M to 25 $\mu$M resveratrol are beneficially employed for toxicity characterization. Moreover, concentrations of 100 $\mu$M crocin and 1 $\mu$M resveratrol are beneficially employed to investigate synergistic effects against light-induced phototoxicity with a final DMSO concentration of 0.1%. Beneficially, DMSO is added to cultures at 0.1% (v/v) as a solvent control.

The experimental tests showed some significant characteristics:

(i) for dosage regimes claimed for the present invention, it would appear that the composition has no adverse toxicity effects on the cell culture;

(ii) the composition is capable of reducing cell death and improving cell longevity; and (iii) there are clear indications of synergistic benefits arising from a combination of crocin and resveratrol which is not provided when these substances are administered individually.

Further details for implementing the aforesaid method of performing experimental tests will now be elucidated. For preparing the cell culture medium, primary RPE cells from three human donors (44, 59 and 71 years old, obtained 3 to 10 hours postmortem) without any history of eye disease were obtained from the Eye Bank of Ludwig Maximilian University. Dulbecco-modified Eagle medium (DMEM, obtainable from Biochrom, Berlin, Germany) supplemented with 10% fetal calf serum (FCS, obtainable from Biochrom, Berlin, Germany) was used as the cell culture medium when undertaking the experimental tests.

The inventors have appreciated in respect of the experimental tests that an increased accumulation of lipofuscin is a common characteristic of ageing RPE cells in vivo and lipofuscin is known to act as a photosensitizer. For example, lipofuscin has been implicated in the development and progression of AMD. Thus, the inventors of the present invention have appreciated when investigating effects of compositions in the light-induced phototoxicity on human RPE that it is desirable to employ primary RPE cells for obtaining representative results of aforesaid effects. All RPE cell cultures investigated by the inventors of the present invention provided pigmented granules in phase-contract microscopy, wherein these granules include, in addition to melanin and other pigments, an amount of lipofuscin. However, this characteristic disappears when RPE cells are cultured for long-term periods.

When undertaking aforesaid experimental tests on cell cultures, RPE cells are beneficially seeded in 35-mm diameter tissue culture dishes and cultured on confluence in darkness. RPE cells are beneficially kept for 24 hours in serum-free conditions. In addition, crocin, resveratrol, or a combination of crocin and resveratrol is beneficially added to the cell cultures for a period of 48 hours. Thereafter, the cells are beneficially washed with phosphate-buffered saline (PBS) solution and then subjected to illumination for 60 minutes to investigate phototoxicity. Immediately after illumination, the PBS is beneficially replaced with serum-free culture medium.

The aforesaid illumination is beneficially obtained from a spot-light source (LC-8, obtainable from Hamamatsu Photonics, Japan), although other illumination sources are optionally employed. This aforesaid spot-light source includes a Mercury-Xenon lamp equipped with an optical fibre as a light guide having a spectral transmission range of 400 nm to 700 nm. When implementing aforesaid illumination of the cell cultures, the cell culture medium is beneficially replaced with RPS just before illumination, plastic covers of cell culture wells are beneficially removed, and cells are beneficially illuminated from above. An illumination intensity of 300 mW/cm$^2$ is beneficially employed for 60 minutes as aforesaid. For obtaining accurate experimental measurements, the illumination power and spectral range of illumination employed for the tests are beneficially measured using a spectrometer (C10083MD, obtainable from Hamamatsu Photonics), although other measuring instruments may be optionally employed. As aforesaid, directly after illumination, PBS applied to the cell cultures is beneficially replaced with serum-free cell culture medium and cells of the cell culture are then subsequently kept in darkness for a further 24 hours. Thereafter, a methylthiotetrazole (MTT) assay is beneficially performed as will next be elucidated.

For determining cell survival rate after the aforesaid illumination, the tetrazolium dye-reduction assay (MTT); 3-[4,5-methylthiazol-2-yl]-2,2-diphenyl tetrazolium bromide) is beneficially used for determining the cell survival rate after aforesaid illumination has been applied. The MTT test, which is contemporarily well-established for the assessment of cell viability, is beneficially performed as described by Mosmann et al. (see: Kemt M, Neubauer A S, Liegl R, Eibl K H, Alge C S, Lackerbauer C A, et al.; "Cytoprotective effects of a blue light-filtering intraocular lens on human retinal pigment epithelium by reducing phototoxic effects on vascular endothelial growth factor-alspha, Bax and Bcl-2 expression", *J. Cataract Refract Surg* 2009; 35(2): pp. 354-362). The serum-free cell culture medium is beneficially removed, the cells then washed with PBS, and thereafter 1000 μL of MTT solution (1.5 mL MTT stock, 2 mg/mL in PBS, together with 28.5 mL MEM) added to each well in the cell culture. Then, the RPS cells are beneficially incubated at 37° C. for 1 hour. As a result of such steps, formazan crystals are formed in the cell culture; the formazan crystals are beneficially dissolved by adding 1000 μL DMSO per well. Thereafter, absorption is beneficially measured by employing a scanning multiwell spectrophotometer operating at an interrogating radiation wavelength of 550 nm (apparatus obtainable from Molecular Probes). Results are thereby obtainable from the method, which are expressible as a mean percentage of proliferation in respect of a control.

The inventors of the present invention have performed the aforesaid experimental tests on crocin, resveratrol and a combination of crocin and resveratrol. On account of crocin being a principal active ingredient of saffron, the experiments results are reasonably considered to pertain also to synergistic combinations of resveratrol and saffron. Results from the experimental tests are beneficially expressed as units of mean absorbance +/− SD for the MTT assay and, for example, ten individual samples per group measured in triplicate. Thereafter, a relative difference between the control and composition-test groups of cells was computed by employing Wilcoxon paired testing with alpha-correction for multiple-testing using SPSS version 13.0 statistical analysis software. When studying results from the aforesaid experimental tests, $p<0.05$ was considered statistically significant when considering efficacy of the compositions tested.

In respect of toxicity testing, both substances, crocin and resveratrol, showed no significant toxic effects in respect of aforesaid RPE cell cultures after 24 hours of exposure at tested concentration. Crocin was employed in a dose regime of 10 μM to 500 μM, resveratrol in a dose regime of 0.1 μM to 25 μM, and a combination of crocin and resveratrol (crocin: 40 μM to 150 μM; resveratrol 0.5 μM to 2.5 μM). As determined from a Wilcoxon-type statistical analysis with a correction for multiple testing, no significant decrease in cellular viability of RPE cells was detected for any of the substances or combinations tested, compared with a control.

In respect of testing effects of crocin and resveratrol on the viability of RPE cells after light exposure, when cells were illuminated with unfiltered light at an intensity of 300 mW/cm$^2$ for 60 min, a significant reduction of RPE cell viability was detected as illustrated in FIG. 3. In FIG. 3, an abscissa axis 200 denotes the control 210 (Co 60), crocin only 220 (C 60), resveratrol only 230 (R 60), and finally a combination of crocin and resveratrol 240. An ordinate axis 250 corresponds to a metabolic activity of RPE cells, namely a percent of mitchondrial dehydrogenase activity. Pre-treatment of cells with either 100 μM crocin or 1 μM resveratrol, or a combination of 100 μM crocin and 1 μM resveratrol, leads to a significantly smaller decrease in viability compared with cells that are not treated with tested substances. Moreover, as denoted by 240, the protective effect provided by a combination 100 μM crocin and 1 μM resveratrol provided best results, namely best protection via synergistic effect against cell damage.

The decrease in viability of primary human RPE cells after illumination with plain white light and after incubation with 100 μM crocin, 1 μM resveratrol, or a combination of both these tested substances, was significantly reduced in comparison to the control. Moreover, in respect of the present invention, the protective effect of the combined treatment using both crocin and resveratrol was significantly stronger than treatment with crocin alone of resveratrol alone after 60 minutes of cell illumination.

As elucidated in the foregoing, saffron is a valuable source of crocin. Beneficially, when a combination of saffron and resveratrol is employed, the crocin content in the saffron is beneficially at least 0.1%, more preferably at least 1%, and more preferably at least 10%. Three major metabolites provide the unique colour and flavour to the saffron stigmas. Picrocrocin ($C_{16}H_{26}O_7$) is considered to be the main bitter principal of saffron. It is a monoterpene glycoside precursor of safranal ($C_{10}H_{14}O$), namely the volatile oil responsible for the aroma of saffron. β-Glucosidase action on picrocrocin liberates the aglycon, 4-hydroxy-2,6,6-trimethyl-1-cyclohexene-1-carboxaldehyde (HTTC, $C_{10}H_{16}O_2$) which is transformed to safranal by dehydration during the drying process of the saffron plant material. A broad range of crocin concentrations in saffron has been found, wherein reported proportions of crocins varies from 0.85% to 32.4% dry weight (Alonso et al.). However, in the aforesaid tests, it was crocin, which is known for its retinal protective effects, that was tested, not specifically safranal.

When preparing dietary supplements pursuant to the present invention, mixtures of resveratrol, for example trans-resveratrol, and saffron are beneficially employed, or mixtures of crocin and resveratrol, wherein crocin has been extracted and purified, for example from saffron. Other components in saffron potentially further enhance benefits provided by embodiments of the present invention. Beneficially, other antioxidant substances can be added to the saffron and resveratrol, alternatively crocin and resveratrol can be employed in combination. Optionally, the crocin and resveratrol are manufactured synthetically by bioengineered processes involving microbial action, fermentation processes and similar. Optionally, embodiments of the present invention can be implemented by way of a sub-cutaneous implants and/or topical skin patches, although oral consumption of compositions pursuant to the present invention by way of syrup, tablets, powders and similar is most preferred, namely as a food supplement. More optionally, when implementing the present invention, a combination of resveratrol and crocin is employed, optionally with other synergistic ingredients such as lutein, ascorbic acid (vitamin C), Omega-3 oils and similar.

Although, the synergistic combination of saffron and resveratrol, alternatively crocin and resveratrol for example, is described in the foregoing in respect of providing a dietary supplement for preventing or treating AMD, the synergistic combination is also capable of assisting with addressing neuron damage in other parts of the human body. The synergistic combination is beneficially of use for preventing and/or treating one or more of the following:

(a) age-related hearing loss, for example due to nerve cell degradation with age occurring in the auditory nerve linking the human ear to the human brain; such benefit can also address and/or prevent tinnitus arising from nerve cell decay and/or damage occurring along the auditory nerve, for example arising from viral infection and/or excessive mobile telephone use;

(b) Alzheimer's disease caused by nerve cell decay in the human brain;

(c) Parkinson's disease caused by motor neuron cell decay; for example the synergistic combination of saffron and resveratrol can be administered as a dietary supplement together with JUMEX™ and/or Levedopa for reducing the progressing of Parkinson's disease;

(d) loss of cognitive ability, for example the synergistic combination of saffron and resveratrol can be provided as a dietary supplement for improving memory and cognition, especially amongst elderly people where problems of cognitive ability are especially noticeable;

(e) mental depression, for example where problems arise from insufficient brain processing ability for coping with complex cognitive problems which then become overwhelming, resulting in a mentally depressed condition;

(f) conditions associated with insulin resistance, for example type-II diabetes, and lack of sense of touch at human body peripheral regions, for example underside of feet causing difficulties walking and balancing, as a result of neurone degeneration associated with type-II diabetes; and (g) conditions associated with high body mass index (BMI) and visceral fat, for example reduction of visceral fat, for calorie restriction, for weight management and for use as an agent for anti-obesity; in certain parts of the World, for example the USA, obesity is an acute problem which results in numerous health problems later in human life, for example in respect of early onset of diabetes, in respect plaque in the human blood supply system which can risk an occurrence of stroke.

In a case of alternative uses (a) to (g) above of compositions pursuant to the present invention, dose regimes may need to be altered to different ranges than most optimal for treating AMD.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

APPENDIX: REFERENCES

Auguud C, Chakravarthy U, Young I, Vioque J, de Jong P T, Bentham G, Rahu M, Seland J, Soubrane G, Tomazzoli L, Topouzis F, Vingerling J R, Fletcher A S, 2008, "Oily fish consumption, dietary docosahexaenoic acid and eicosapentaenoic acid intakes, and associations with neovascular age-related macular degeneration", Am J Clin Nutr 88(2): pp. 398-406.

Bathaie S Z, Mousavi S Z, 2010, "New Applications and Mechanisms of Action of Saffron and its Important Ingredients", Crit Rev Food Sci Nutr, 50: pp. 761-786.

Brooks C L, Gu W, 2009, "Anti-aging protein SIRT1: a role in cervical cancer?" Aging (Albany N.Y.) 1(3): pp. 279-280.

Cangemi F E, 2007, "TOZAL Study: An open case control study of an oral antioxidant and omega-3 supplement for dry AMD", *BMC Ophthalmology* 7: pp. 3-12.

Chong E W, Kreis A J, Wong T Y, Simpson J A, Guymer R H, 2008, "Dietary omega-3 fatty acid and fish intake in the primary prevention of age-related macular degeneration: a systematic review and meta-analysis", Arch Ophthalmol 126(6): pp. 826-833.

Chong E W, Robman L D, Simpson J A, Hodge A M, Aung K Z, Dolphin T K, English D R, Giles G G, Guymer R H, 2009, "Fat consumption and its association with age-related macular degeneration", Arch Ophthalmol 127 (5): pp. 674-680.

Chucair A J, Rotstein N P, Sangiovanni J P, During A, Chew E Y, Politi L E, 2007, "Lutein and zeaxanthin protect photoreceptors from apoptosis induced by oxidative stress: relation with docosahexaenoic acid", Invest Ophthalmol Vis Sci 48(11): pp. 5168-5177.

Elliot P J, Jirousek M, 2008, "Sirtuins novel targets for metabolic diseases", Curr Opin Investig Drugs 9(4): pp. 371-378.

Falsini B, Piccardi M, Minnella A, Savastano C, Capoluongo E, Fadda A, Balestrazzi E, Maccarone R, Bisti S, "Saffron Supplementation Improves Retinal Flicker Sensitivity in Early Age-Related Macular Degeneration", Invest Ophthalmol Vis Sci 51(12): pp. 6118-6124.

Huang L L, Coleman H R, Kim J, de Monasterio F, Wong W T, Schleicher R L, Ferris F L 3$^{rd}$, Chew E Y, 2008, "Oral supplementation of lutein/zeaxanthin and omega-3 long chain polyunsaturated fatty acids in persons aged 60 years or older, with or without AMD", Invest Ophthalmol Vis Sci 49(9): pp. 3863-3869.

Johnson E J, Chung H Y, Caldarella S M, Snodderly D M, 2008, "The influence of supplemental lutein and docosahexaenoic acid on serum, lipoproteins, and macular pigmentation", Am J Clin Nutr 87(5): pp. 1521-1529.

Jones A A, 2007, "Age related macular degeneration—should your patients be taking additional supplements?", Aust Fam Physician 36(12): pp. 1026-1028.

Joseph J, Cole G, Head E, Ingram D, 2009, "Nutrition, brain aging, and neurodegeneration", J Neurosci 29(41): pp. 12795-12801.

Khan A A, Dace D S, Ryazanov A G, Kelly J, Apte R S, 2010, "Resveratrol regulates pathologic angiogenesis by a eukaryotic elongation factor-2 kinase-regulated pathway", Am J Pathol 177(1): pp. 481-492.

Kim W T, Suh E S, 2010, "Retinal protective effects of resveratrol via modulation of nitric oxide synthase on oxygen-induced retinopathy", Korean J Ophthalmol 24(2): pp. 108-118.

Kim E J, Um S J, 2008, "SIRT1: roles in aging and cancer", BMB Rep. 41(11): pp. 751-756.

King R E, Bomser J A, Min D B, 2006, "Bioactivity of Resveratrol", Comprehensive Reviews in Food Science and Food Safety 5: pp. 65-70.

Kubota S, Kurihara T, Mochimaru H, Satofuka S, Noda K, Ozawa Y, Olike Y, Ishida S, Tsubota K, 2009, "Prevention of ocular inflammation in endotoxin-induced uveitis with resveratrol by inhibiting oxidative damage and nuclear factor-kappaB activation", Invest Ophthalmol Vis Sci 50(7): pp. 3512-3519.

Laabich A, Vissvesvaran G P, Lieu K L, Murata K, McGinn T E, Manmoto C C, Sinclair J R, Karliga I, Leung D W, Fazwi A, Kubota R, 2006, "Protective effect of crocin against blue light- and white light-mediated photoreceptor cell death in bovine and primate retinal primary cell culture", Invest Ophthalmol Vis Sci 47(7): pp. 3156-3163.

Lagouge M, Argmann C, Gerhart-Hines Z, Meziane H, Lerin C, Daussin F, Messadeq N, Milne J, Lambert P, Elliot P, Geny B, Laakso M, Puigserver P, Auwerx J, 2006, "Resveratrol improves mitochondrial function and protects against metabolic disease by activating SIRT1 and PGC-1alpha", a reported by Cell 127(6): pp. 1109-1122.

Lavu S, Boss, Elliot P J, 2008, "Sirtuins—novel therapeutic targets to treat age-associated diseases", Nat Rev Drug Discov 7(10): pp. 841-853.

Maccarone R, Di Marco S, Bisti S, 2008, "Saffron supplement maintains morphology and function after exposure to damaging light in mammalian retina", Invest Ophthalmol Vis Sci 49(3): pp. 1254-1261.

Maraini G, Williams S L, Sperduto R D, Ferris F L, Milton R C, Clemns T E, Rosmini F, Ferrigno L, 2009, "Effects of multivitamin/mineral supplementation on plasma levels of nutrients", Report No. 4 of the Italian-American clinical trial of nutritional supplements and age-related cataract", Ann 1st Super Sanita 45(2): pp. 119-127.

Natoli R, Zhu Y, Valter K, Bisti S, Eells J, Stone J, 2010, "Gene and noncoding RNA regulation underlying photoreceptor protection: microarray study of dietary antioxidant saffron and photobiomodulation in rat retina", Mol Vis, 16: pp. 1801-1822.

Pillarisetti S, 2008, "A Review of Sirt1 and Sirt1 Modulators in Cardiovascular and Metabolic Diseases", Recent Patents on Cardiovascular Drug Discovery 3(3): pp. 157-164.

Queen B L, Tollefsbol T O, 2010, "Polyphenols and aging", Curr Aging Sci 3(1): pp. 34-42.

Richer S, Stiles W, Thomas C, 2009, "Molecular medicine in ophthalmic care", Optometry 80(12): pp. 695-701.

Rotstein N P, Politi L E, German O L, Girotti R, 2003, "Protective effect of docosahexaenoic acid on oxidative stress-induced apoptosis of retina photoreceptors", Invest Ophthalmol Vis Sci, 44(5): pp. 2252-2259.

Sangiovanni J P, Agrön E, Clemens T E, Chew E Y, 2009, "Omega-3 long-chain polyunsaturated fatty acid intake is inversely associated with 12-year progression to advanced AMD", Arch Ophthalmol 127(1): pp. 110-112.

Sangiovanni J P, Chew E Y, Agrön E, Clemons T E, Ferris 3$^{rd}$, Gensler G, Lindblad A S, Milton R C, Seddon J M, Klein R, Sperduto R D, 2008, "The relationship of dietary omega-3 long-chain polyunsaturated fatty acid intake with incident age-related macular degeneration AREDS report no. 23, Arch Ophthalmo 125(9): pp. 1274-1279.

Sangiovanni J P, Chew E Y, Clemons T E, Davis M D, Ferris F L 3$^{rd}$, Gensler G R, Kurinij N, Lindblad A S, Milton R C, Seddon J M, Sperduto R D, 2007, "The relationship of dietary lipid intake and age-related macular degeneration in a case-control study: AREDS Report No. 20, Arch Ophthalmo 125(5): pp. 671-679.

Sheu S J, Liu N C, Chen J L, 2010, "Resveratrol protects human retinal pigment epithelial cells from acrolein-induced damage", J Ocul Pharmacol Ther 26(3): pp. 231-236.

Smith J J, Kenney R D, Gagne D J et al., 2009, "Small molecule activators of SIRT1 replicate signalling pathways triggered by calorie restriction in vivo", BMC Syst Biol 3: pp. 31.

Tan J S, Wang J J, Flood V, Mitchell P., 2009, "Dietary fatty acids and the 10-year incidence of age-related macular degeneration: the Blue Mountains Eye Study", Arch Ophthalmol 127(5): pp. 656-665.

Thornton J, Edwards R, Mitchell P, Harrison R A, Buchan I, Kelly S P, 2005, "Smoking and age-related macular degeneration: a review of association", Eye 19: pp. 935-944.

Tuo J, Ross R J, Herzlich A A, Shen D, Ding X, Zhou M, Coon S L, Hussein N, Salem N Jr, Chan C C, 2009, "A high omega-3 fatty acid diet reduces retinal lesions in a murine model of macular degeneration", Am J Pathol 175(2): pp. 799-807.

Valenzano D R, Terzibasi E, Genade T, Cattaneo A, Domenici L, Cellerino A, 2006, "Resveratrol prolongs lifespan and retards the onset of age-related markers in a short-lived vertebrate", Curr Biol 6(3): pp. 296-300.

Zheng Y, Liu Y, Ge J, Wang X, Liu L, Bu Z, Liu P, 2010, "Resveratrol protects human lens epithelial cells against H2O2-induced oxidative stress by increasing catalase, SOD-1, and HO-1 expression", Mol Vis 16: pp. 1467-1474.

The invention claimed is:

1. A composition comprising an age-related macular-degeneration inhibiting effective amount of a combination of resveratrol and saffron wherein the effective amount is formulated as 100 mg resveratrol and 20 mg saffron stigma wherein said saffron stigma is in the form of a powder.

2. The composition as claimed in claim 1, wherein the saffron has a crocin content of 0.1% to 10%.

3. The composition as claimed in claim 1, wherein said composition additionally includes: lutein, zeaxanthin, vitamin C, vitamin E, zinc, cupric citrate, and vitamin A acetate.

4. The composition as claimed in claim 3, wherein said vitamin C is provided in a form of ascorbic acid.

5. The composition as claimed in claim 1 arranged in liquid-form, powder-form, capsule-form or tablet-form.

6. A pack including a plurality of tablets or capsules including a composition as claimed in claim 1, wherein said pack includes said tablets or capsules disposed in manner together with graphical markings to assist users to consume a recommended dose of the composition over a period of duration extending over a plurality of days.

* * * * *